US006593345B1

(12) United States Patent
Bryant et al.

(10) Patent No.: US 6,593,345 B1
(45) Date of Patent: Jul. 15, 2003

(54) NAPHTHYL COMPOUNDS, INTERMEDIATES, COMPOSITIONS, AND METHODS OF USE

(75) Inventors: Henry Uhlman Bryant, Indianapolis, IN (US); Thomas Alan Crowell, Indianapolis, IN (US); Charles David Jones, Indianapolis, IN (US); Alan David Palkowitz, Carmel, IN (US)

(73) Assignee: Eli Lilly and Company, Indianapolis, IA (US)

( * ) Notice: Subject to any disclaimer, the term of this patent is extended or adjusted under 35 U.S.C. 154(b) by 0 days.

(21) Appl. No.: 08/921,625

(22) Filed: Aug. 27, 1997

Related U.S. Application Data

(60) Provisional application No. 60/025,125, filed on Aug. 29, 1996.

(51) Int. Cl.[7] .................. A61K 31/535; C07D 295/02; C07D 421/00; C07D 207/30
(52) U.S. Cl. .................. 514/319; 514/231.2; 514/427; 514/539; 514/567; 544/107; 546/207; 548/562; 560/37; 564/336
(58) Field of Search .............. 514/231.2, 319, 514/427, 539, 567; 544/107; 546/207; 548/562; 560/37; 564/336

(56) References Cited

U.S. PATENT DOCUMENTS

| 3,274,213 A | 9/1966 | Lednicer | 260/326.5 |
|---|---|---|---|
| 3,277,106 A | 10/1966 | Bencze et al. | 260/295 |
| 3,394,125 A | 7/1968 | Crenshaw | 260/326.5 |
| 3,413,305 A | 11/1968 | Crenshaw | 260/326.5 |
| 4,133,814 A | 1/1979 | Jones et al. | 260/326 |
| 4,230,862 A | 10/1980 | Suarez et al. | 546/237 |
| 4,358,593 A | 11/1982 | Jones et al. | 546/202 |
| 4,380,635 A | 4/1983 | Peters | 546/202 |
| 4,418,068 A | 11/1983 | Jones et al. | 546/237 |
| 5,395,842 A | 3/1995 | Labrie | 514/320 |
| 5,470,854 A | 11/1995 | Angerer t al. | 514/233 |
| 5,472,962 A | 12/1995 | Koizumi et al. | 514/233.5 |
| 5,484,795 A | 1/1996 | Bryant et al. | 514/319 |
| 5,510,357 A | 4/1996 | Palkowitz | 514/324 |
| 5,567,712 A | * 10/1996 | Palkowitz | 514/231.2 |
| 5,574,190 A | * 11/1996 | Palkowitz | 568/440 |
| 5,998,401 A | * 12/1999 | Palkowitz | 514/212 |
| 6,268,361 B1 | * 7/2001 | Palkowitz | 514/231.2 |
| 6,509,356 B1 | 1/2003 | Dodge et al. | 514/319 |

FOREIGN PATENT DOCUMENTS

| EP | 062 503 | 10/1982 |
|---|---|---|
| WO | WO 89/0289 | 4/1989 |
| WO | WO 95/10513 | 4/1995 |
| WO | WO 96/21656 | 7/1996 |

OTHER PUBLICATIONS

Crenshaw, R.R., et al, J. Med. Chem. 14(12):1185–1190 (1971).
Jones, C.D., et al, J. Med. Chem. 27: 1057–1066) 1984.
Jones, C.D., et al, J. Med. Chem. 35: 931–938 1992.
Korobka, et al., Chemical Abstracts, 106:32507u, 1987.
Ruenitz et al., J. Med. Chem., 25:1056–1060 (1982).
Jordan et al., Molecular Pharmacology, 26:272–278 (1984).
Foster et al., J. Med. Chem., 28:1491–1497 (1985).
Loser et al., Eur. J. cancer Clin. Oncol., 21:985–990 (1985.

* cited by examiner

Primary Examiner—Richard L. Raymond
Assistant Examiner—Tamthom N. Truong
(74) Attorney, Agent, or Firm—Gary M. Birch; Gilbert T. Voy

(57) ABSTRACT

The instant invention provides novel substituted naphthyl compounds, intermediates, compositions, pharmaceutical formulations, and methods of use.

15 Claims, No Drawings

NAPHTHYL COMPOUNDS, INTERMEDIATES, COMPOSITIONS, AND METHODS OF USE

This application claims the benefit of Provisional Application No. 60/025,125, filed Aug. 29, 1996.

BACKGROUND OF THE INVENTION

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

In response to the clear need for new pharmaceutical agents which are capable of alleviating the symptoms of, inter alia, postmenopausal syndrome, the present invention provides naphthyl compounds, pharmaceutical formulations thereof, and methods of using such compounds for the treatment of postmenopausal syndrome and other estrogen-related pathological conditions such as those mentioned below.

Thus, it would be a significant contribution to the art to provide novel substituted naphthyl compounds useful, for example, in the inhibition, treatment, or prevention of the disease states as indicated herein.

SUMMARY OF THE INVENTION

The present invention provides compounds of formula I:

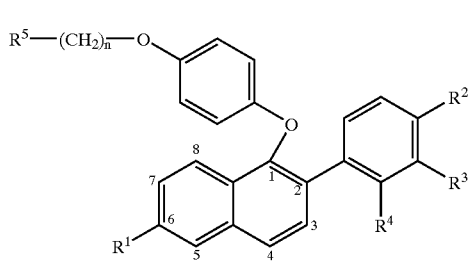

wherein
$R^1$ is —H, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl);

$R^2$ is —H, —F, —Cl, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —OSO$_2$ ($C_4$–$C_6$ alkyl);

$R^3$ and $R^4$ are, independently, —H, —F, —Cl, —CH$_3$, —OH, —O($C_1$–$C_4$ alkyl), —OCOAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl), with the proviso that both $R^3$ and $R^4$ cannot be hydrogen;

n is 2 or 3; and $R^5$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino;

or a pharmaceutically acceptable salt or solvate thereof.

Also provided by the present invention are intermediate compounds which are useful for preparing the pharmaceutically active compounds of the present invention.

The present invention further provides pharmaceutical formulations containing compounds of formula I, optionally containing an effective amount of an additional therapeutic agent selected from the group consisting of estrogen, progestin, bisphosphonate, parathyroid hormone (PTH), and subcombinations thereof. The present invention also provides methods of use of the compounds of formula I.

DETAILED DESCRIPTION OF THE INVENTION

Intermediate compounds useful in the synthesis of compounds of formula I are also provided, and include compounds of formula II:

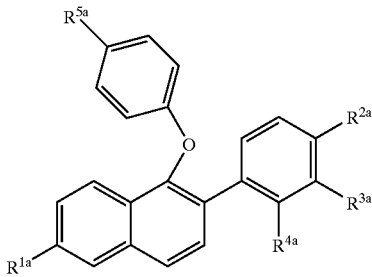

II wherein:
$R^{1a}$ is —H or —$OR^6$ in which $R^6$ is a hydroxy protecting group;
$R^{2a}$ is —H, —F, —Cl, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —(CO)O($C_1$–$C_6$ alkyl), or —OSO$_2$($C_4$–$C_6$ alkyl);
$R^{3a}$ is —H, —F, —Cl, or —$OR^7$ in which $R^7$ is a hydroxy protecting group;
$R^{4a}$ is —H, —F, —Cl, —CH$_3$, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —OSO$_2$ ($C_4$–$C_6$ alkyl), with the proviso that both $R^{3a}$ and $R^{4a}$ cannot be hydrogen;
$R^5$ is —OH, —COW, or —O(CO)W; and
W is —H or $C_1$–$C_6$ alkyl;
or a pharmaceutically acceptable salt or solvate thereof.

Still further provided by the present invention are intermediate compounds of formula III which are useful for preparing the pharmaceutically active compounds of the present invention:

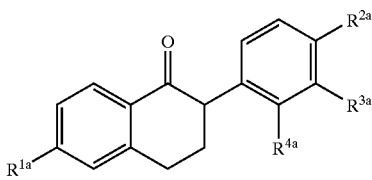

III wherein:
$R^{1a}$ is —H or —$OR^6$ in which $R^6$ is a hydroxy protecting group;
$R^{2a}$ is —H, —F, —Cl, —OH, —O($C_1$–$C_4$ alkyl), —OCOAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl);
$R^{3a}$ and $R^{4a}$ are, independently, —H, —F, —Cl, —CH$_3$, —OH, —O($C_1$–$C_4$ alkyl), —OCOAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl), with the proviso that both $R^{3a}$ and $R^{4a}$ cannot be hydrogen.

Additionally provided by the present invention are intermediate compounds of formula IV which are useful for preparing the pharmaceutically active compounds of the present invention:

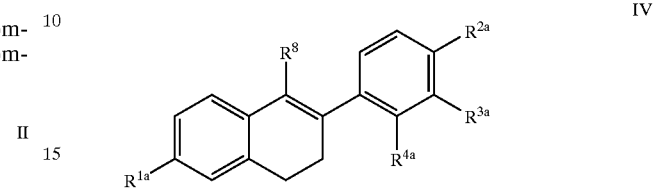

IV wherein:
$R^{1a}$ is —H or —$OR^6$ in which $R^6$ is a hydroxy protecting group;
$R^{2a}$ is —H, —F, —Cl, —OH, —O($C_1$–$C_4$ alkyl), —OCOAr where Ar is phenyl or substituted phenyl, —OCO($C_1$–$C_6$ alkyl), —O(CO)O($C_1$–$C_6$ alkyl), or —OSO$_2$ ($C_4$–$C_6$ alkyl);
$R^{3a}$ is —H, —F, —Cl, or —OR in which $R^7$ is a hydroxy protecting group;
$R^{4a}$ is —H, —F, —Cl, —CH$_3$, —OH, —O($C_1$–$C_4$ alkyl), —OCOAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl), with the proviso that both $R^{3a}$ and $R^{4a}$ cannot be hydrogen;
$R^8$ is —OH or —OCO($C_1$–$C_6$ alkyl);
wherein the dotted line represents optional unsaturation;
or a pharmaceutically acceptable salt or solvate thereof.

Also provided by the present invention are intermediate compounds of formula VI which ate useful for preparing the pharmaceutically active compounds of the present invention:

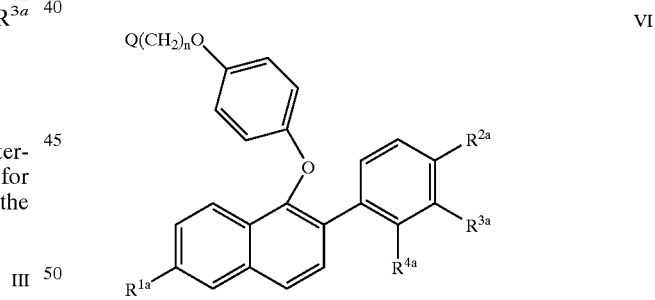

VI wherein:
$R^{1a}$ is —H or —$OR^6$ in which $R^6$ is a hydroxy protecting group;
$R^{2a}$ is —H, —F, —Cl, —OH, —O($C_1$–$C_4$ alkyl), —OCOAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl);
$R^{3a}$ is —H, —F, —Cl, or —$OR^7$ in which $R^7$ is a hydroxy protecting group;
$R^{4a}$ is —H, —F, —Cl, —CH$_3$, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl), with the proviso that both $R^{3a}$ and $R^{4a}$ cannot be hydrogen; and Q is a leaving group;
or a pharmaceutically acceptable salt or solvate thereof.

General terms used in the description of compounds herein described bear their usual meanings. For example, "$C_1$–$C_4$ alkyl" refers to straight or branched aliphatic chains of 1 to 4 carbon atoms including methyl, ethyl, propyl, iso-propyl, n-butyl, and the like; and "$C_1$–$C_6$ alkyl" encompasses the groups included in the definition of "$C_1$–$C_4$ alkyl" in addition to groups such as pentyl, iso-pentyl, hexyl, and the like.

The term "substituted phenyl" refers to a phenyl group having one or more substituents selected from the group consisting of $C_1$–$C_4$ alkyl, $C_1$–$C_3$ alkoxy, hydroxy, nitro, chloro, fluoro, tri(chloro or fluoro)methyl, and the like. "$C_1$–$C_4$ alkoxy" refers to a $C_1$–$C_4$ alkyl group attached through an oxygen bridge, such as methoxy, ethoxy, n-propoxy, and isopropoxy, butoxy, and the like. Of these $C_1$–$C_4$ alkoxy groups, methoxy is highly preferred.

The term "inhibit" includes its generally accepted meaning which includes prohibiting, preventing, restraining, and slowing, stopping, or reversing progression, severity, or ameliorating a resultant symptom or effect.

Preferred embodiments of the current invention are 1-[4-[2-(1-piperidinyl)ethoxy]phenoxy]-2-(3-hydroxyphenyl)-6-hydroxynaphthalene hydrochloride, for example, where $R^1$ and $R^3$ are hydroxy, $R^5$ is piperidinyl, and the hydrochloride salt thereof; and 1-[4-[2-(1-piperidinyl)ethoxy]phenoxy]-2-(3-methoxyphenyl)-6-hydroxynaphthalene hydrochloride, for example, where $R^1$ is hydroxy, $R^3$ is methoxy, $R^5$ is piperidinyl, and the hydrochloride salt thereof.

Illustrative compounds of the present invention include but are not limited to the following:

1-[4-[2-(1-piperidinyl)ethoxy]phenoxy]-2-(3-methoxyphenyl)-6-methoxynaphthalene hydrochloride,
1-[4-[2-(1-piperidinyl)ethoxy]phenoxy]-2-(3-methoxyphenyl)naphthalene hydrochloride,
1-[4-[2-(1-piperidinyl)ethoxy]phenoxy]-2-(3-hydroxyphenyl)-6-hydroxynaphthalene hydrochloride,
1-[4-[2-(1-piperidinyl)ethoxy]phenoxy]-2-(3-hydroxyphenyl)naphthalene hydrochloride,
1-[4-[2-(1-piperidinyl)ethoxy]phenoxy]-2-(3-hydroxyphenyl)-6-methoxynaphthalene hydrochloride, and
1-[4-[2-(1-piperidinyl)ethoxy]phenoxy]-2-(3-methoxyphenyl)-6-hydroxynaphthalene hydrochloride.

The starting material for preparing compounds of the present invention are compounds of formula III:

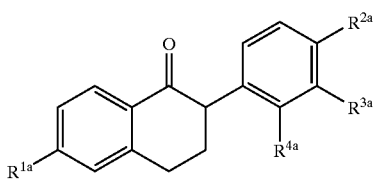

III wherein:

$R^{1a}$ is —H or —$OR^5$ in which $R^5$ is a hydroxy protecting group;

$R^{2a}$ is —H, —F, —Cl, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —$OSO_2$($C_4$–$C_6$ alkyl);

$R^{3a}$ and $R^{4a}$ are, independently, —H, —F, —Cl, —$CH_3$, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —$OSO_2$($C_4$–$C_6$ alkyl), with the proviso that both $R^{3a}$ and $R^{4a}$ cannot be hydrogen.

Compounds of formula III are well known in the art and are prepared essentially as described by Boyle et al., in U.S. Pat. No. 4,910,212 which is herein incorporated by reference. See, also, Collins, D. J., et al., *Aust. J. Chem.*, 41:745–756 (1988); and Collins, D. J., et al., *Aust. J. Chem.*, 37:2279–2294 (1984).

In preparing compounds of the present invention, generally, a ketone of formula III is aromatized, providing a phenol of formula IVc, which is then reacted with a 4-halobenzaldehyde to give a biaryl ether of formula IIa, which, in turn, is converted to a phenol of formula IIb. This synthetic route is as shown below in Scheme I, and $R^{1a}$, $R^{2a}$, $R^{3a}$, and $R^{4a}$ are as defined above.

Scheme I

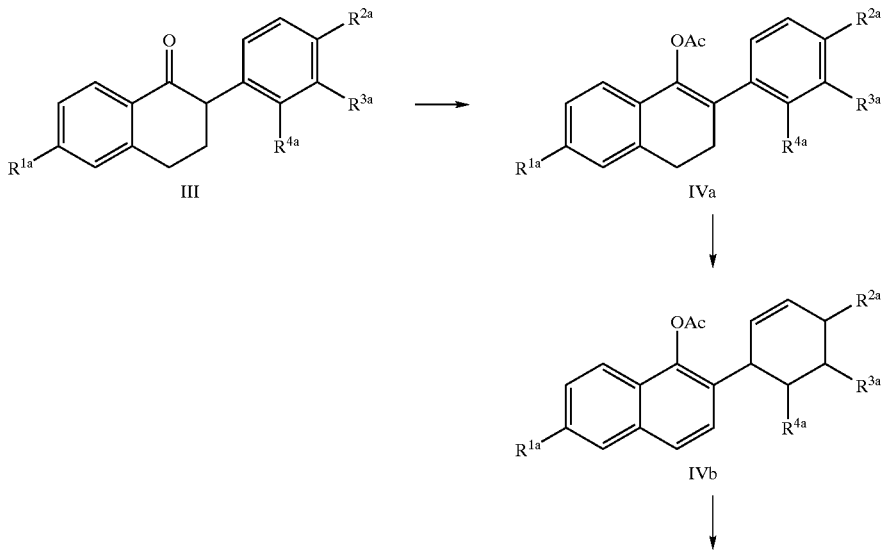

-continued

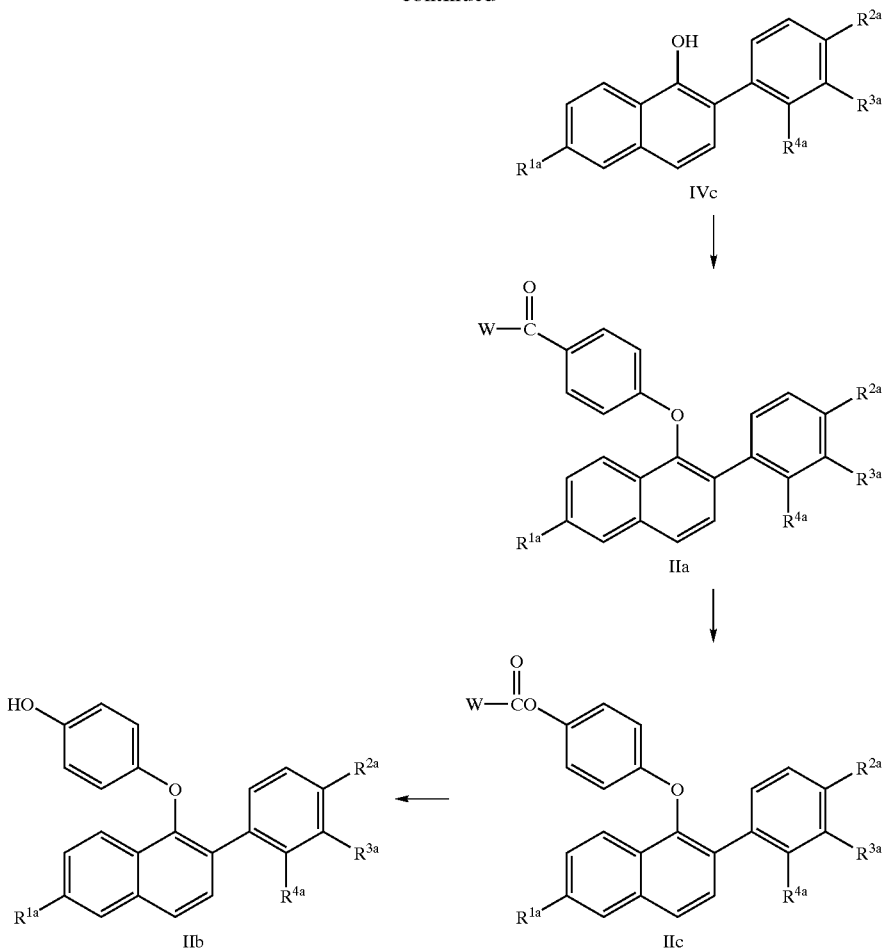

In the first step of the present process, a compound of formula III is converted to a phenol of formula IVc via a three-step protocol, essentially as described by Wang, G., et al., *M. Syn. Commun.,* 21:989 (1991). In essence, a formula III ketone is enolized by refluxing a solution of an acetylenolic ester solvent, in the presence of an acid catalyst. The resulting enolacetate is directly converted to a naphtholacetate which is then hydrolyzed to a phenol of formula IVc.

In converting a ketone of formula III to its respective enol acetate, various known acid catalysts can be used. Preferably, non-aqueous acids, and particularly, p-toluenesulfonic acid is preferred. A preferred acetylenolic ester solvent would be isopropenyl acetate.

When run at reflux, the present reaction takes from about 6 to about 48 hours to complete. The enol product from this reaction is not isolated, but upon completion of the reaction, the resulting solution is treated with an appropriate oxidant and heated to reflux for, optimally, about 1 to about 3 hours.

Appropriate oxidants for this second phase of the first reaction step shown in Scheme I are limited to those known in the art which can lead to the elimination of hydrogen from a saturated system to give an aromatized system. Such oxidants include, for example, de-hydrogenation catalysts such as platinum, palladium, and nickel, elemental sulfur and selenium, and quinones. For the present application, quinone oxidants, especially 2,3-dichloro-5,6-dicyano-1,4-benzoquinone (DDQ) are preferred. About 1 to 2 equivalents of DDQ per equivalent of substrate will drive the present process phase.

The resulting product of the present phase, a 1-naphtholester, is then subjected to hydrolysis to provide a compound of formula IVc, thus completing the first process step shown in Scheme I. The present hydrolysis phase is accomplished via either acid or basic hydrolysis of the substrate in a polar protic solvent such as water or one or more solvents containing an alcohol such as methanol or ethanol. A cosolvent such as tetrahydrofuran (THF) or dioxane also may be added to the solution to aid solubility. Appropriate bases for this phase include sodium hydroxide, potassium hydroxide, lithium hydroxide, and the like. Appropriate acids include, for example, hydrochloric acid, methanesulfonic acid, p-toluenesulfonic acid, and the like. A preferred acid would be hydrochloric acid.

This final phase of the first step shown in Scheme I, supra, can be run at ambient temperature and runs in a short period of time, typically from 1 to about 12 hours. Completion of the present reaction can be determined via standard chromatographic techniques such as thin layer chromatography.

In the second step of Scheme I, a phenol of formula IVc is first reacted with a base, followed by the addition of a 4-halobenzaldehyde or 4-halobenzoketone, in a polar aprotic solvent, under an inert atmosphere such as nitrogen, to give a biarylether of formula IIa. This reaction is well known in the art and is carried out essentially as described by Yeager, G. W., et al., *Synthesis,* 63 (1991).

More particularly, 1 equivalent of a formula IVc compound is first treated with at least 1 equivalent of an alkali metal hydride or carbonate in an appropriate solvent, followed by a dropwise addition of a 4-halobenzaldehyde in the same solvent as used with the substrate. Appropriate solvents for this reaction are those solvents or mixture of solvents which remain inert throughout the reaction. N,N-dimethylformamide (DMF), especially the anhydrous form thereof, is preferred. Preferably, sodium hydride is used as the required base, and 4-fluorobenzaldehyde is used as the preferred 4-halobenzaldehyde.

The temperature employed in this step of the present process should be sufficient to effect completion of this reaction, without encouraging the formation of undesirable by-products. A preferred temperature range for this reaction is from about 30° C. to about 100° C. Under preferred reaction conditions, a formula IIa compound will be prepared via the preferred process in about 24 to about 48 hours.

The final reaction shown in Scheme I, the conversion of the aldehyde moiety of a formula IIa compound to a phenol group, thus forming a compound of formula IIb, is known in the art as a Bayer-Villiger oxidation. See, e g., Fiesers, L., et al., *Reagents for Organic Synthesis*, 1:467, Wiley (N.Y. 1967); Hassall, C. H., Organic Reactions, 9:73–106 (Wiley, N.Y. 1967).

In general, the present reaction involves the combination of a benzaldehyde with a peracid such as peracetic acid or m-chloroperbenzoic acid in an inert solvent such as chloroform or methylenechloride. The product of this reaction, a formate ester, can then be readily hydrolyzed to the desired phenol. See, for example, Yeager, et al., supra; Godfrey, I. M., et al., *J. Chem. Soc. Perkins. Trans. I*:1353 (1974); and Rue, R., et al., *Bull. Soc. Shim. Fr.,* 3617 (1970).

For the present reaction, a preferred variation is described by Matsumoto, M., et al., *J. Org. Chem.,* 49:4741 (1984). This method involves combining a benzaldehyde of formula IIa with at least 1 to about 2 equivalents of 30% hydrogen peroxide in an alcohol solvent, and in the presence of a catalytic acid. Under these conditions, the phenol is formed directly, and the need for an additional hydrolysis step is, therefore, eliminated. The preferred solvent and acid catalyst for the present reaction is methanol and concentrated sulfuric acid, respectively. Under the preferred reaction conditions, the transformation from a formula IIa compound to a formula IIb compound is complete after stirring for about 12 to about 48 hours at ambient temperatures.

Compounds of formula II, IIa, and IIb are useful as intermediate compounds in the preparation of pharmaceutically active compounds of formula I of the present invention. Upon preparation of a formula IIb compound, it is reacted with a compound of formula V $$R^5—(CH_2)_n—Q \quad\quad\quad V$$

wherein $R^5$ and n are as defined above, and Q is a leaving group, such as, for example, mesylate, tosylate, chloro, or bromo, with bromo being preferred, to form a compound of formula Ia. The formula Ia compound is then deprotected, when $R^6$ and/or $R^7$ hydroxy protecting groups are present, to form a compound of formula Ib. These process steps are shown in Scheme II below.

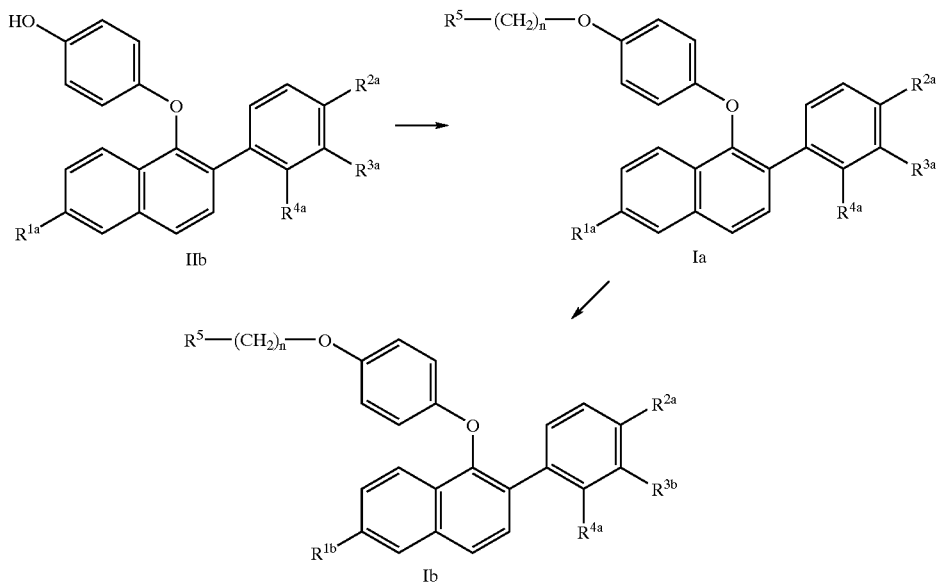

wherein:
$R^{1a}$, $R^{2a}$, $R^{3a}$, $R^{4a}$, $R^5$, and n are as defined above;
$R^{1b}$ is —H or —OH;
$R^{3b}$ is —H, —OH, or —F, or —Cl,
or a pharmaceutically acceptable salt or solvate thereof.

In the first step of the process shown in Scheme II, the alkylation-is carried out via standard procedures. Compounds of formula V are commercially available or are prepared by means well known to one of ordinary skill in the art. Preferably, the hydrochloride salt of a formula V compound, particularly 2-chloroethylpiperidine hydrochloride, is used.

Generally, at least about 1 equivalent of formula IIb substrate are reacted with 2 equivalents of a formula V compound in the presence of at least about 4 equivalents of an alkali metal carbonate, preferably cesium carbonate, and an appropriate solvent. Solvents for this reaction are those solvents or mixture of solvents which remain inert throughout the reaction. N,N-dimethylformamide, especially the anhydrous form thereof, is preferred. The temperature employed in this step should be sufficient to effect completion of this alkylation reaction. Typically, ambient temperature is sufficient and preferred. The present reaction preferably is run under an inert atmosphere, particularly nitrogen.

Under the preferred reaction conditions, this reaction will run to completion in about 16 to about 20 hours. The progress of the reaction may be monitored via standard chromatographic techniques.

As an alternative for preparing compounds of formula Ia, a formula IIb compound is reacted with an excess of an alkylating agent of formula VII as further illustrated in Scheme III below:

Q'—(CH$_2$)$_n$—Q    VII wherein n is 2 or 3, and Q' and Q each are the same or different leaving groups, in an alkali solution.

amine, or an inorganic base, such as, K$_2$CO$_3$, Cs$_2$CO$_3$, and the like. Preferably, the hydrochloride salt of piperidine is reacted with the alkylated compound of formula IIb in an inert solvent, such as anhydrous DMF, with Cs$_2$CO$_3$, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run to completion. Of course, the progress of this reaction step can be monitored via standard chromatographic techniques.

Hydroxy compounds of formula I are obtained by cleaving, when present, the R$^6$ and R$^7$ hydroxy protecting groups of formula Ia compounds via well known procedures. Numerous reactions for the formation and removal of

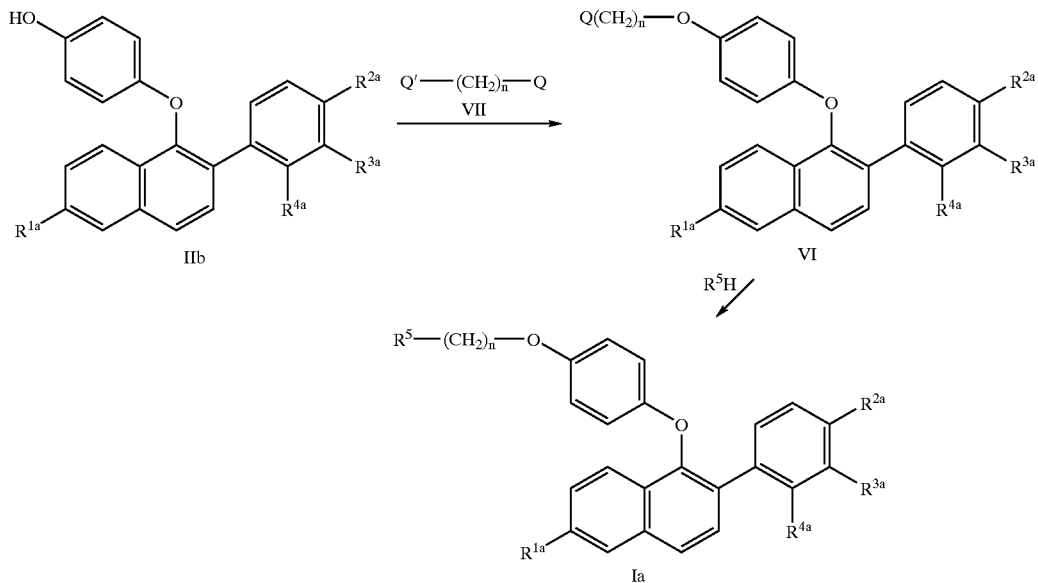

wherein R$^{1a}$, R$^{2a}$, R$^{3a}$, R$^{4a}$, R$^5$, and n are as defined above.

Appropriate leaving groups include sulfonates, such as methanesulfonate, 4-bromobenzenesulfonate, toluenesulfonate, ethanesulfonate, isopropylsulfonate, 4-methoxybenzenesulfonate, 4-nitrobenzenesulfonate, 2-chlorobenzenesulfonate, triflate, and the like, halogens such as bromo, chloro, and iodo, and other related leaving groups. Halogens are preferred leaving groups and bromo is especially preferred.

A preferred alkali solution for this alkylation reaction contains potassium carbonate in an inert solvent such as, for example, methylethyl ketone (MEK) or DMF. In this solution, the 4-hydroxy group of the benzoyl moiety of a formula IIb compound exists as a phenoxide ion which displaces one of the leaving groups of the alkylating agent.

This reaction is most favorable when the alkali solution containing the reactants and reagents is brought to reflux and allowed to run to completion. When using MEK as the preferred solvent, reaction times run from about 6 hours to about 20 hours. The reaction product from this step is then reacted with an equivalent or excess of 1-piperidine, 1-pyrrolidine, methyl-1-pyrrolidine, dimethyl-1-pyrrolidine, 4-morpholine, dimethylamine, diethylamine, or 1-hexamethyleneimine, via standard techniques, to form compounds of formula Ia. The reaction may be facilitated with the addition of a strong base, such as, a tertiary alkyl such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for nonregioselective removing preferred R$^6$ and/or R$^7$ hydroxy protecting groups, particularly methyl, are essentially as described in Examples 2 and 4, infra.

Compounds of formula I in which R$^1$ and R$^3$ are methoxy and hydroxy, respectively, are obtained by selective cleavage of the 3'-methoxy group (see: Example 5, infra). In general, the procedure for cleavage of a methoxy group on the 3' position involves the combination of the 6-, 3'-dimethoxy substrate with a demethylation reagent chosen from the group of boron tribromide, boron trichloride or boron triiodide or with AlCl$_3$ and various thiol reagents, such as EtSH. The reaction is conducted under an inert atmosphere such as nitrogen, with one or more moles of the reagent per mole of methoxy group to be cleaved. Appropriate solvents for this reaction are those solvents or mixture of solvents which remain inert throughout the demethylation reaction. Halogenated solvents such as dichloromethane, 1,2-dichloroethane, and chloroform, or aromatic solvents such as benzene or toluene are preferred. The temperature employed in this reaction of the present process should be sufficient to effect completion of the demethylation reaction. However, it is advantageous to keep the temperature below 0° C. in order to maximize selectivity for cleavage of the 3'-methoxy group and avoid the formation of undesirable byproducts especially the product 6,3'-dihydroxy analog arising from excessive demethylation. Under the preferred reaction conditions, a selectively dealkylated product will be formed after stirring the reaction for about 1 to 24 hours. A preferred variation involves the use of boron tribromide in the amount of approximately 1.5 moles with one mole of the 6-, 3'-dimethoxy substrate in dichloromethane under a nitrogen atmosphere at a temperature of −20° C. for 1 to 4 hours.

Compounds of formula I in which $R^1$ and $R^3$ are hydroxy and methoxy, respectively are prepared by a complimentary regioselective cleavage of the 6-methoxy group (see: Example 6, infra). The procedure for regioselective cleavage of a methoxy group on the 6-position involves the combination of the 6-, 3'-dimethoxy substrate with a demethylation reagent chosen from the group of alkali metal thioalkyl compounds, such as sodium thiomethylate, lithium thiomethylate, sodium thioethylate, lithium thioethylate, sodium 2-propanethiolate, lithium 2-methylpropane-2-thiolate, thiolate, and the like. The reaction is conducted under an inert amosphere such as nitrogen, with one or more moles of the reagent per mole of methoxy group to be cleaved. Appropriate solvents for this reaction are those solvents or mixture of solvents which remain inert throughout the demethylation reaction. Solvents which facilitate bimolecular nucleophilic displacement reactions, such as N,N-dimethylformamide (DMF), N,N-dimethylacetamide (DMAC), dimethylsulfoxide (DMSO), or N-methylpyrrolidinone (NMP), especially the anhydrous forms therof, are preferred. Anhydrous N,N-dimethylformamide is especially preferred. A temperature of about 80 to 120° C. is required to effect completion of the demethylation reaction. However, it is necessary to minimize the temperature in order to maximize selectivity for cleavage of the 6-methoxy group while avoiding the formation of undesirable byproducts and especially the 6-, 3'-dihydroxy compound that would arise from excessive demethylation. Under the preferred reaction conditions, a selectively dealkylated product will be formed after stirring the reaction for about 2 to 8 hours. A preferred variation involves the use of lithium thioethylate in the amount of approximately 15 moles with one mole of the 6-, 3'-dimethoxy substrate in anhydrous DMF under a nitrogen atmosphere at a temperature of 107° C. for 5 hours.

Other preferred compounds of formula I are prepared by replacing the 6- and/or 3'-position hydroxy moieties, when present, with a moiety of the formula —O—CO—($C_1$-$C_6$ alkyl), or —O—$SO_2$—($C_4$-$C_6$ alkyl) via well known procedures. See, for example, U.S. Pat. No. 4,358,593. When an —O—CO($C_1$-$C_6$ alkyl) group is desired, a mono- or dihydroxy compound of formula I is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, for example, Haslam, et al., *Tetrahedron*, 36:2409–2433 (1980).

The present reactions are carried out at moderate temperatures, in the range from about −25° C. to about 100° C., frequently under an inert atmosphere such as nitrogen gas. However, ambient temperature is usually adequate for the reaction to run. Acylation of a 6-position and/or 3'-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R^1$ and/or $R^3$ groups of formula I compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, for example, *Bull. Chem. Soc. Japan*, 38:1979 (1965), and *Chem. Ber.*, 788 and 2024 (1970).

Each of the above techniques which provide —O—CO—($C_1$-$C_6$ alkyl)moieties are carried out in solvents as discussed above. Those techniques which do not produce an acid product in the course of the reaction do not call for the use of an acid scavenger in the reaction mixture. When a formula I compound is desired in which the 6- and/or 3'-position hydroxy group of a formula I compound is converted to a group of the formula —O—$SO_2$—($C_4$-$C_6$ alkyl), the mono- or dihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). Such reactions are carried out under conditions such as provided above in the discussion of reaction with acid halides and the like.

The term "solvate" represents an aggregate that comprises one or more molecules of the solute, such as a formula I compound, with one or more molecules of solvent. Although the free-base form of formula I compounds can be used in the methods of the present invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The present invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the present invention which is capable of inhibiting, alleviating, ameliorating, treating, or preventing further symptoms in mammals, including humans, suffering from estrogen deprivation, for example, menopause or ovariectomy, or inappropriate estrogen stimulation such as uterine fibrosis or endometriosis, or suffering from aortal smooth muscle cell profileration or restenosis. In the case of estrogen-dependent cancers, the term "effective amount" means the amount of compound of the present invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissollution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to treat, inhibit, or prevent the symptoms and/or disease of a mammal, including humans, suffering from the above maladies according to this invention will depend upon the particular disease, symptoms, and severity. Dosage, routes of administration, and frequency of dosing is best decided by the-attending physician. Generally, accepted and effective doses will be from 15 mg to 1000 mg, and more typically from 15 mg to 80 mg. Such dosages will be administered to a patient in need of treatment from one to three times each day or as often as needed for efficacy, and for periods of at least two months, more typically for at least six months, or chronically.

As a further embodiment of the invention, the compounds of formula I may be administered along with an effective amount of an additional therapeutic agent, including but not limited to estrogen, progestin, benzothiophene compounds having including raloxifene, naphthyl compounds having antiestrogen activity, bisphosphonate compounds such as alendronate and tiludronate, parathyroid hormone (PTH), including truncated and/or recombinant forms of PTH such as, for example, PTH (1–34), calcitonin, bone morphogenic proteins (BMPs), or combinations thereof. The different forms of these additional therapeutic agents available as well as the various utilities associated with same and the applicable dosing regimens are well known to those of skill in the art.

Various forms of estrogen and progestin are commercially available. As used herein, the term "estrogen" includes compounds having estrogen activity and estrogen-based agents. Estrogen compounds useful in the practice of the present invention include, for example, estradiol estrone, estriol, equilin, equilenin, estradiol cypionate, estradiol valerate, ethynyl estradiol, polyestradiol phosphate, estropipate, diethylstibestrol, dienestrol, chlorotrianisene, and mixtures thereof. Estrogen-based agents, include, for example, 17-α-ethynyl estradiol (0.01–0.03 mg/day), mestranol (0.05–0.15 mg/day), and conjugated estrogenic hormones such as Premarin® (Wyeth-Ayerst; 0.2–2.5 mg/day). As used herein, the term "progestin" includes compounds having progestational activity such as, for example, progesterone, norethynodrel, norgestrel, megestrol acetate, norethindrone, progestin-based agents, and the like. Progestin-based agents include, for example, medroxyprogesterone such as Provera® (Upjohn; 2.5–10 mg/day), norethylnodrel (1.0–10.0 mg/day), and norethindrone (0.5–2.0 mg/day). A preferred estrogen-based compound is Premarin®, and norethylnodrel and norethindrone are preferred progestin-based agents. The method of administration of each estrogen- and progestin-based agent is consistent with that known in the art.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1: Gelatin Capsules

| Ingredient | Quantity (mg/capsule) |
|---|---|
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2: Tablets

| Ingredient | Quantity (mg/tablet) |
|---|---|
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
|---|---|
| Active Ingredient | 0.25 |
| Ethanol | 29.75 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
|---|---|
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension
Suspensions each containing 0.1–1000 mg of a compound of formula I per 5 mL dose.

| Ingredient | Weight |
|---|---|
| Active Ingredient | 0.1–1000 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following examples and preparations are provided to better elucidate the practice of the present invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which his invention pertains.

EXAMPLES

NMR data for the following Examples were generated on a GE 300 MHz NMR instrument, and anhydrous d-6 DMSO was used as the solvent unless otherwise indicated.

Preparation 1

2,4-di-(3-methoxyphenyl)butyric Acid

A solution of 50.68 g (305 mmol) of 3-methoxyphenylacetic acid in 1.4 L of anhydrous THF was prepared and cooled to −70° C. under a nitrogen atmosphere. Slowly, 400 mL of 1.6 M (640 mmol) of n-butyl lithium was added and the solution was allowed to stir for two hours at −70° C. A solution of 72.1 g (335 mmol) of 2-(3-methoxyphenyl)ethylbromide in 100 mL of THF was added and the reaction was allowed to proceed for sixteen hours, while slowly warming to ambient temperature. The solvent was removed by evaporation in vacuo. The residue was dissolved in a solution of 50 mL of 5 N NaOH and 450 mL of water and stirred for one hour. The aqueous solution was extracted three times with ether. The aqueous solution was acidified with the addition of 150 mL of 5 N HCl and the product extracted three times with $CHCl_3$. The organic extracts were combind, washed with brine and dried by filtration through anhydrous $Na_2SO_4$. The solvent was removed by evaporation. This yielded 90 g of the title compound as a clear oil.

Preparation 2

2-(3-Methoxyphenyl)-6-methoxy-1-tetralone

A solution of 90 g (300 mmol) of 2,4-di-(3-methoxyphenyl)butyric acid in 1.5 L of $CH_2Cl_2$ was prepared and 62.4 g (300 mmol) of PCl$_5$ was slowly added. The reaction mixture was refluxed under a nitrogen atmosphere for four hours. The solvent was removed by evaporation. The residue was slurried with 100 mL of aqueous NaHCO$_3$ and the slurry extracted three times with CHCl$_3$. The combined organic extracts was washed with brine, dried with Na$_2$SO$_4$, and evaporated to dryness. The product was crystallized from 2-propanol at −70° C. and then twice from MeOH at −70° C. This yielded 65 g of the title compound as a tan solid, mp 81–82° C.

Preparation 3

1-Acetyloxy-2-(3-methoxyphenyl)-6-methoxy-3,4-dihydronaphthalene

A suspension was prepared of 47 g (167 mmol) of 2-(3-methoxyphenyl)-6-methoxy-1-tetralone and 4.7 g of p-toluenesulfonic acid mono-hydrate in 470 mL of iso-propenylacetate. The reaction mixture was refluxed for forty-eight hours under a nitrogen atmosphere. The reaction was allowed to cool and 10 g of NaHCO$_3$ was added, the solution was poured into 500 mL of an aqueous solution of NaHCO$_3$. The aqueous solution was extracted three times with 200 mL portions of EtOAc. The combined organic extract was washed with brine, dried with Na$_2$SO$_4$, and evaporated to a dark oil. This yielded 52.7 g of the title compound.

Preparation 4

1-Acetyloxy-2-(3-methoxyphenyl)-6-methoxynaphthalene

A solution was prepared of 52.7 g (162 mmol) of 1-acetyloxy-2-(3-methoxyphenyl)-6-methoxy-3,4-dihydronaphthalene and 36.9 g (162 mmol) of DDQ in 500 mL of p-dioxane. The solution was heated to reflux for two hours under a nitrogen atmosphere. The reaction was allowed to cool and the solvent removed by evaporation. The residue was extracted by stirring in CHCl$_3$ for sixteen hours, then filtering to remove the insoluble material. The CHCl$_3$ extract was further purified by chromatography on a silica gel column eluted with CHCl$_3$. This resulted in a red oil, which was suspended in MeOH and crystallized at −70° C. This yielded 46.5 g of the title compound as a low melting solid.

Preparation 5

1-Hydroxy-2-(3-methoxyphenyl)-6-methoxynaphthalene

A suspension was prepared of 46.5 g of 1-acetyloxy-2-(3-methoxyphenyl)-6-methoxynaphthalene and 40 mL of 5N HCl in 400 mL of MeOH. The reaction mixture was heated to reflux for eleven hours. The reaction mixture was evaporated to a clear oil. This yielded 38.6 g of the title compound.

PMR: (CDCl$_3$) 8.19 ppm (d, J=9.1 Hz, 1H); 7.51–6.94 ppm (m, 8H); 5.91 ppm (s, 1H); 3.94 ppm (s, 3H)

MS: m/e=280 (M) FD

EA: Calc. for C$_{18}$H$_{16}$O$_3$: C, 77.12; H, 5.75 Found: C, 76.91; H, 5.81.

Preparation 6

1-Hydroxy-2-(3-methoxyphenyl)naphthalene

In a manner analogous to Preparations 1–5, the title compound was prepared.

PMR: 8.30 ppm (m, 1H); 7.80 ppm (m, 1H); 7.57–7.45 ppm (m, 4H); 7.40 ppm (d, J=7.1 Hz, 1H); 7.35 ppm (d, J=6.0 Hz, 1H); 7.06 ppm (s, 1H0; 6.97 ppm (dd, J=6.0 Hz, 1H); 6.00 ppm (s, 1H); 3.90 ppm (s, 1H)

MS: m/e=250 (M) FD

EA: Calc. for C$_{17}$H$_{14}$O$_2$-0.21 mol EtOAc: C, 79.52; H, 5.93 Found: C, 79.72; H, 5.63.

Preparation 7

1-(4-Formylphenoxy)-2-(3-methoxyphenyl)-6-methoxynaphthalene

A solution was prepared of 9.8 g (35 mmol) of 1-hydroxy-2-(3-methoxyphenyl)-6-methoxynaphthalene in 490 mL of DMF under a nitrogen atmosphere and to this solution was slowly added 1.47 g (36.8 mmol) of 60% NaH in mineral oil. After ten minutes, 7.5 mL (70 mmol) of 4-fluorobenzaldehdye was added and the reaction mixture was heated to 70° C. for sixty-four hours. The reaction mixture was evaporated to dryness and the residue partioned between water and EtOAc. The EtOAc layer was dried with Na$_2$SO$_4$ and chromatographed on a silica gel column eluted with EtOAc-hexane (1:9)(v/v). The final product was further purified by crystallization from MeOH. This yielded 2.4 g of the title compound as a tan solid, mp 145–146° C.

PMR: (CDCl$_3$) 9.80 ppm (s, 1H); 7.79 ppm (d, J=9.2 Hz, 1H); 7.75 ppm (d. J=8.8 Hz, 1H); 7.67 ppm (d, J=8.9 Hz, 2H); 7.58 ppm (d, J=8.4 Hz, 1H); 7.31–7.05 ppm (m, 5H); 6.86–6.75 ppm (m, 3H); 3.95 ppm (s, 3H); 3.72 ppm (s, 3H)

MS: m/e=384 (M) FD

EA: Calc. for C$_{25}$H$_{20}$O$_4$: C, 78.11; H, 5.24 Found: C, 78.26; H, 5.33.

Preparation 8

1-(4-Formylphenoxy)-2-(3-methoxyphenyl)naphthalene

In a manner similar to that used in Preparation 7, the title compound was prepared.

PMR: (CDCl$_3$) 9.90 ppm (s, 1H); 7.90–7.83 ppm (m,2H); 7.70 ppm (d, J=8.0 Hz, 1H); 7.35–7.20 ppm (m, 4H); 7.58–7.43 ppm (m, 2H); 7.58 ppm (d, J=8.4 Hz, 1H); 7.10 ppm (m, 2H); 6.80 ppm (d, J=8.0 Hz, 2H); 3.80 ppm (s, 3H)

MS: m/e=354 (M) FD

EA: Calc. for C$_{24}$H$_{18}$O$_3$-0.2 mol EtOAc: C, 86.06; H, 5.31 Found: C, 80.17; H, 5.29.

Preparation 9

1-(4-Hydroxyphenoxy)-2-(3-methoxyphenyl)-6-methoxynaphthalene 2.3 g (6 mmol) of 1-(4-formylphenoxy)-2-(3-methoxyphenyl)-6-methoxynaphthalene was suspended in 15 mL of MeOH and 1.7 mL (9 mmol) of 30% H$_2$O$_2$ was added. To the stirring mixture, 0.76 mL of conc. H$_2$SO$_4$ was slowly added. An additional 30 mL of MeOH was added and the reaction was allowed to proceed for forty-eight hours. The reaction was neutralized with NaHCO$_3$ solution and extracted with CHCl$_3$. The CHCl$_3$ was washed with brine, dried with Na$_2$SO$_4$, and chromatographed on a silica gel column eluted with CHCl$_3$. This yielded 1.6 g of the title compound as a tan amorphous powder, mp 125–126° C.

PMR: 8.9 ppm (s,1H); 7.78 ppm (d,J=8.1 Hz, 1H); 7.70 ppm (d, J=9.0 Hz, 1H); 7.57 ppm (d, J=8.4 HZ, 1H); 7.39 ppm (t, J=9.0 Hz, 1H); 7.19–7.05 (m, 3H); 6.80 ppm (d, J=8.9 Hz, 1H); 6.50 ppm (q, J=8.9 Hz, 4H); 3.85 ppm (s, 3H); 3.64 ppm (s, 3H)

MS: m/e=372 (M) FD

EA: Calc. for $C_{24}H_{20}O_4$: C, 77.40; H, 5.41 Found: C, 77.69; H, 5.30.

Preparation 10

1-(4-Hydroxyphenoxy)-2-(3-methoxyphenyl) naphthalene

In a manner similar to that used in Preparation 9, the title compound was prepared and isolated as a clear oil.

PMR: (CDCl$_3$) 7.90 ppm (d, J=8.0 Hz, 1H); 7.87 ppm (d, J=7.0 Hz, 1H); 7.80 ppm (d, J=8.0 Hz, 1H); 7.60 ppm (d, J=8.0 Hz, 1H); 7.50–7.40 ppm (m, 3H); 7.10 ppm (m, 2H); 6.80 ppm (d, J=8.0 Hz, 1H); 6.60 ppm (s, 4H); 4.40 ppm (s, 1H); 3.70 ppm (s, 3H)

MS: m/e=342 (M) FD

EA: Calc. for $C_{23}H_{18}O_3$-0.5 mol EtOAc: C, 77.70; H, 5.74 Found: C, 77.93; H, 5.82.

Example 1

1-[4-[2-(1-piperidinyl)ethoxy]phenoxy]-2-(3-methoxyphenyl)-6-methoxynaphthalene hydrochloride A solution of 1.5 g (4 mmol) of 1-(4-hydroxyphenoxy)-2-(3-methoxyphenyl)-6-methoxynaphthalene in 40 mL of DMF was prepared. To this solution was added 920 mg (5 mmol) of 2-chloroethylpiperidine hydrochloride and 5.2 g (16 mmol) of Cs$_2$CO$_3$, the reaction was stirred at ambient temperature under a nitrogen atmosphere for sixteen hours. The solvents were removed by evaporation and the residue partioned between water and EtOAc. The EtOAc layer was washed with water, then brine, dried with Na$_2$SO$_4$, and evaporated to dryness. The residue was dissolved in 10 mL of MeOH ane 1 mL of 5N HCl was added. The solvents were removed by evaporation and the product crystallized from EtOAc. This yielded 1.8 g of the title compound as a white solid, mp 161–162° C.

PMR: 10.43 ppm (bs, 1H); 7.81 ppm (d, J=8.3 Hz, 1H); 7.67 ppm (d, J=9.0 Hz, 1H); 7.59 ppm (dd, J=8.8, 1.1 Hz, 1H); 7.41 ppm (d, s, 1H); 7.24 ppm (t, J=7.8 Hz, 1H); 7.18–7.06 ppm (m, 3H); 6.88–6.75 ppm (m, 3H); 6.59 ppm (dd, J=8.8, 1.1 Hz, 2H); 4.22 ppm (t, J=4.3 Hz, 2H); 3.85 ppm (s, 3H); 3.65 ppm (s, 3H); 3.47–3.22 ppm (m, 4H); 2.98–2.79 ppm (m, 2H); 1.83–1.57 ppm (m, 5H); 1.39–1.22 ppm (m, 1H)

MS: m/e=483 (M-HCl) FD

EA: Calc. for $C_{31}H_{33}NO_4$—HCl: C, 71.60; H, 6.59; N, 2.69 Found: C, 71.87; H, 6.43; N, 2.76.

Example 2

1-[4-[2-(1-piperidinyl)ethoxy]phenoxy]-2-(3-methoxyphenyl)naphthalene hydrochloride In a manner similar to that used in Example 1, the title compound was prepared and isolated as a white crystalline powder, mp 145° C.

PMR: (CDCl$_3$) 7.90 ppm (dd, J=8.0 Hz, 2H); 7.80 ppm (d, J=9.0 Hz, 1H); 7.60 ppm (d, J=8.0 Hz, 2H); 7.48–7.44 ppm (m, 3H); 7.20 ppm (d, J=7.0 Hz, 2H); 7.10 ppm (d, J=7.0 Hz, 2H); 6.80 ppm (d, J=9.0 Hz, 1H); 6.60 ppm (s, 3H); 4.40–4.30 ppm (m, 2H); 3.70 ppm (s, 3H), 3.60–3.50 ppm (m, 1H); 3.20 ppm (m, 2H); 2.80–2.60 ppm (m, 2H); 2.30–2.10 ppm (m, 2H); 1.90–1.80 ppm (m, 3H); 1.70–1.60 ppm (m, 2H); 1.50–1.30 ppm (m, 1H)

MS: m/e=453 (M-HCl) FD

EA: Calc. for $C_{30}H_{31}NO_3$—HCl: C, 73.53; H, 6.58; N, 2.86 Found: C, 73.31; H, 6.73; N, 3.05.

Example 3

1-[4-[2-(1-piperidinyl)ethoxy]phenoxy]-2-(3-hydroxyphenyl)-6-hydroxynaphthalene hydrochloride A solution was prepared of 1.5 g (2.9 mmol) of 1-[4-[2-(1-piperidinyl)ethoxy]phenoxy]-2-(3-methoxyphenyl)-6-methoxynaphthalene hydrochloride in 30 mL of CH$_2$Cl$_2$ and the solution was cooled to 0° C. under a nitrogen atmosphere. To this solution was added 1.09 mL (2.89g, 11.5 mmol) of BBr$_3$ and the reaction was allowed to proceed for two hours at 0° C. The reaction was quenched by the addition of aqueous NaHCO$_3$ solution (50 mL). The reaction mixture was extracted with CHCl$_3$. The organic layer was washed with brine, dried with Na$_2$SO$_4$, and evaporated to dryness. The residue was suspended in THF and filtered. To the filtrate was added 1 mL of 5N HCl and the solvents were removed by evaporation. This yielded 0.99 g of the title compound as a tan amorphous powder.

PMR: 9.90 ppm (s, 1H0; 9.88 ppm (bs, 1H); 9.3 ppm (s, 1H); 7.65 ppm (d, J=8.4 Hz, 1H0; 7.60 ppm (d, J=8.8 Hz, 1H); 7.45 ppm (d, J=8.7 Hz, 1H); 7.17 ppm (s, 1H); 7.14–7.01 ppm (m, 2H); 6.99–6.92 ppm (m, 2H); 6.77 ppm (d, J=8.9 Hz, 2H); 6.68–6.54 ppm (m, 3H); 4.18 ppm (t, J=4.7 Hz, 2H); 3.47–3.18 ppm (m, 4H); 2.98–2.81 ppm (m, 2H); 1.81–1.58 ppm (m, 5H); 1.38–1.22 ppm (m, 1H)

MS: m/e=455 (M-HCl) FD

EA: Calc. for $C_{29}H_{29}NO_4$—HCl: C, 70.80; H, 6.15; N, 2.85 Found: C, 70.68; H, 6.29; N, 2.65.

Example 4

1-[4-[2-(1-piperidinyl)ethoxy]phenoxy]-2-(3-hydroxyphenyl)naphthalene hydrochloride In a manner similar to that used in Example 3, the title compound was prepared and isolated as a white crystalline solid, mp 194–195° C.

PMR: (MeOD-d$_4$) 7.96–7.84 ppm (m, 2H); 7.80 ppm (d, J=8.0 Hz, 1H); 7.50 ppm (d, J=8.0 Hz, 1H); 7.50–7.40 ppm (m, 3H); 7.12–7.09 ppm (dd,J=8.0 Hz, 1H); 7.00–6.90 ppm (m, 2H); 4,70 ppm (s, 1H); 4.20–4.10 ppm (m, 1H); 3.50–3.40 ppm (m, 2H); 3.40–3.20 ppm(m, 4H); 1.90–1.70 ppm (m, 4H); 1.80–1.60 ppm (m,2H)

MS: m/e=439 (M-HCl) FD

EA: Calc. for $C_{29}H_{29}NO_3$—HCl: C, 73.17; H, 6.35; N, 2.94 Found: C, 72.88; H, 6.31; N, 2.90.

Example 5

1-[4-[2-(1-piperidinyl)ethoxy]phenoxy]-2-(3-hydroxyphenyl)-6-methoxynaphthalene

A solution of 1-[4-[2-(1-piperidinyl)ethoxy]phenoxy]-2-(3-methoxyphenyl)-6-methoxynaphthalene hydrochloride (0.500 g, 0.96 mmol) in 20 mL of anhydrous methylene chloride under N$_2$ atmosphere was chilled in an acetonitrile-dry ice bath to −20° C. Boron tribromide (1.44 mmol) was added dropwise over 3 minutes by syringe as a 1 M solution (1.44 mL) also in methylene chloride. The resulting mixture was allowed to warm to 0° C. and stirred for 2 hours. The reaction was then poured into a stirring solution of cold saturated sodium bicarbonate (100 mL) and the crude product was extracted with ethyl acetate (4×25 mL). The organic extracts were combined, dried (magnesium sulfate), and concentrated to a oily foam. The crude free base was purified by radial chromatography using 5/95 methanol/methylene chloride. The appropriate fractions were combined and concentrated in vacuo to provide 220 mg (49%) of 1-[4-[2-(1-piperidinyl)ethoxy]-phenoxy]-2-(3-hydroxyphenyl)-6-methoxynaphthalene as a white crystalline solid, mp 170–171° C.

PNMR d 9.36 (s, 1H), 7.77 (d, J=8.6 Hz, 1H), 7.68 (d, J=9.2 Hz, 1H), 7.53 (d, J=8.6 Hz, 1H), 7.39 (d, J=2.4 Hz, 1H), 7.09 (m, 2H), 6.93 (m, 2H), 6.69 (d, J=9.1 Hz, 2H), 6.61 (m, 1H), 6.52 (d, J=9.1 Hz, 2H), 3.84 (t, J=6.0 Hz, 2H), 3.83 (s, 3H), 2.51 (t, J=6.0 Hz, 2H), 2.25–2.40 (m, 4H), 1.35–1.45 (m, 4H), 1.25–1.35 (m, 2H)

MS (FD) m/e 470 (MH+)

Anal. Calc'd. for $C_{30}H_{31}NO_4$: C, 76.73; H, 6.65; N, 2.98. Found: C, 76.94; H, 6.83; N, 3.26.

For determination by PMR analysis of the site of demethylation, treatment of the product in DMSO solution with several equivalents of NaOD in DMSO produced the following changes in chemical shifts: three signals corresponding to the two aromatic protons that are ortho- and one proton that is para- to the hydroxyl group in the 2-aryl moiety were shifted 0.59, 0.57, and 0.75 ppm upfield, respectively. In contrast, the signals attributable to protons on the naphthalene moiety at positions 5 and 7 were only slightly affected (shift<0.2 ppm). The remaining signals in the spectrum of the product in DMSO were essentially unaltered by addition of NaOD. The shifts described above demonstrate that the OH group is positioned on the 2-aryl ring and the remaining methoxy group is on the naphthalene ring (i.e. regioselective selective demethylation occurred at the 2-(3-methoxyphenyl)moiety).

Example 6

1-[4-[2-(1-piperidinyl)ethoxy]phenoxy]-2-(3-methoxyphenyl)-6-hydroxynaphthalene

A solution of ethanethiol (2.85 ml) in anhydrous DMF (125 mL) under $N_2$ atmosphere was cooled in an ice bath and treated dropwise with 20.1 mL of 1.6 M n-BuLi in hexane. The resulting solution, which was approximately 0.22 M in lithium thioethylate (LiSEt) was allowed to warm to ambient temperature prior to its use. To 1-[4-[2-(1-piperidinyl)-ethoxy]phenoxy]-2-(3-methoxyphenyl)-6-methoxynaphthalene hydrochloride (0.550 g, 1.05 mmol) under nitrogen atmosphere was added 70 mL (15.4 mmol) of the LiSEt solution and the resulting reaction mixture was heated in a 107° C. oil bath for 5 hr. The resulting yellow solution was concentrated under reduced pressure to remove most of the solvent and the yellow oil concentrate was distributed between 300 mL of ethyl acetate and 1N HCl (100 mL) to which 50 g of ice had been added. The ethyl acetate layer extract was washed with 4×25 mL portions of brine, dried over magnesium sulfate, filtered, and concentrated to a foul-smelling yellow oil. The crude material was purified in portions by radial chromatography that employed 5% methanol in chloroform as the elution solvent. The appropriate fractions were combined, concentrated, and dried in vacuo to provide 265 mg (53%) of 1-[4-[2-(1-piperidinyl)ethoxy]-phenoxy]-2-(3-methoxyphenyl)-6-hydroxynaphthalene, as a grey foam.

PMR (DMSO-$d_6$) d 9.90 (S, 1H), 7.66 (d, J=8.0 Hz, 1H), 7.63 (d, J=8.6 Hz, 1H), 7.50 (d, J=8.6 Hz, 1H), 7.25–7.16 (m, 2H), 7.10–6.95 (m, 3H), 6.79 (m, 1H), 6.70 (d, J=9.0 Hz, 2H), 6.54 (d, J=9.0 Hz, 2H), 3.86 (t, J=6.0 Hz, 2H), 3.64 (s, 3H), 2.52 (t, J=6.0 Hz, 2H), 2.25–2.40 (m, 4H), 1.35–1.45 (m, 4H), 1.25–1.35 (m, 2H)

MS (FD) m/e 470 (M+)

Anal. Calc'd. for $C_{30}H_{31}NO_4$: C, 76.73; H, 6.65; N, 2.98. Found: C, 75.89; H, 6.81; N, 3.01.

In an experiment similar to that described in Example 5, the site of demethylation was determined by PNMR analysis: treatment of the product in DMSO solution with several equivalents of NaOD in DMSO produced the following changes in chemical shifts: Signals corresponding to the two aromatic protons at positions 5 and 7 of the naphthalene ring (as well as other protons on the naphthalene moiety) were dramatically shifted upfield. In contrast, the signals attributable to protons on the 2-aryl moiety were only slightly affected (shift<0.2 ppm). The remaining signals in the spectrum of the product in DMSO were essentially unaltered by addition of NaOD. The shifts described above demonstrate that the OH group is positioned on the naphthalene ring and the remaining methoxy group is on the 2-aryl moiety (i.e. regioselective selective demethylation occurred at the 7-methoxy group).

The following discussions illustrate methods of use for the compounds of formula I in experimental models or in clinical studies. These examples are for the purposes of illustration and are not meant to be limiting in any way.

A. Osteoporosis

Experimental models of postmenopausal osteoporosis are known in the art. Germane to this invention is the ovariectomized rat model which is provided in U.S. Pat. No. 5,393,763. The compounds of formula I would be active in this model and would demonstrate an effective treatment or prevention of bone loss due to the deprivation of estrogen.

An additional demonstration of the method of treating or preventing osteoporosis due to estrogen deprivation would be as follows: One hundred patients would be chosen, who are healthy postmenopausal women, aged 45–60 and who would normally be considered candidates for estrogen replacement therapy. This includes women with an intact uterus, who have had a last menstrual period more than six months, but less than six years. Patients excluded for the study would be those who have taken estrogens, progestins, or corticosteroids six months prior to the study or who have ever taken bis-phosphonates.

Fifty women (test group) would receive 15–80 mg of a compound of formula I, for example, Formulation 1 (above), per day. The other fifty women (control group) would receive a matched placebo per day. Both groups would receive calcium carbonate tablets (648 mg) per day. The study is a double-blind design. Neither the investigators nor the patients would know to which group each patient is assigned.

A baseline examination of each patient includes quantitative measurement of urinary calcium, creatinine, hydroxyproline, and pyridinoline crosslinks. Blood samples are measured for serum levels of osteocalcin and bone-specific alkaline phosphatase. Baseline measurements would also include a uterine examination and bone mineral density determination by photon absorptiometry.

The study would continue for six months, and each the patients would be examined for changes in the above parameters. During the course of treatment, the patients in the treatment group would show a decreased change in the biochemical markers of bone resorption as compared to the control group. Also, the treatment group would show little or no decrease in bone mineral density compared to the control group. Both groups would have similar uterine histology, indicating the compounds of formula I have little or no utrotrophic effects.

B. Hyperlipidemia

Experimental models of postmenopausal hyperlipidemia are known in the art. Germane to this invention is the ovariectomized rat model which is detailed in U.S. Pat. No. 5,464,845. Data presented in Table 1 show comparative results among ovariectomized rats, rats treated with 17-α-ethynyl estradiol ($EE_2$), and rats treated with certain compounds of this invention. Although $EE_2$ caused a decrease in serum cholesterol when orally administered at 0.1 mg/kg/day, it also exerted a stimulatory effect on the uterus so that $EE_2$ uterine weight was substantially greater than the uterine weight of the ovariectomized animals. This uterine response to estrogen is well recognized in the art.

Not only did the compounds of the present invention reduce serum cholesterol compared to the ovariectomized animals, but the uterine weight was increased to lesser extent than those given $EE_2$. Compared to estrogenic compounds known in the art, the benefit of serum cholesterol reduction while lessening the effect on uterine weight is unusual and desirable.

As expressed in the data below, estrogenicity also was assessed by evaluating the response of eosinophil infiltration into the uterus. The compounds of this invention did not cause as large an increase in the number of eosinophils observed in the stromal layer of the ovariectomized, rat uteri. $EE_2$ caused a substantial and expected increase in eosinophil infiltration.

The data presented in Table 1 reflect the response per treatment group.

TABLE 1

| Compound No. | Dose mg/kg[a] | Uterine weight % Inc[b] | Uterine Eosinophil (Vmax)[c] | Serum Cholest. % Dec.[d] |
|---|---|---|---|---|
| EE2[e] | 0.1 | 138.8* | 174.3* | 88.1* |
| Example 1 | 0.01 | 9.6 | 2.1 | 12.1 |
|  | 0.1 | 21.9 | 4.8 | 55.6* |
|  | 1.0 | 35.8* | 4.8 | 60.5* |
| Example 2 | 0.1 | 42.7* | 4.5 | 59.6* |
| (free base) | 1.0 | 43.8* | 7.8 | 66.2* |
|  | 10.0 | 37.2* | 4.5 | 59.0* |
| Example 3 | 0.1 | 10.4 | 4.8 | 26.3* |
|  | 1.0 | 15.3 | 3.0 | 45.7* |
|  | 10.0 | 3.9 | 1.2 | 22.9 |
| Raloxifene[f] | 0.1 | 23.5 | 5.4 | 49.3* |

[a] mg/kg PO
[b] Uterine Weight % increase versus the ovariectomized controls
[c] Eosinophil peroxidase, $V_{max}$
[d] Serum cholesterol decrease versus ovariectomized controls
[e] 17-α-Ethynyl-estradiol
[f] Raloxifene [2-(4-hydroxyphenyl)-6-hydroxybenzo[b]thien-3-yl] [4-[2-(1-piperidinyl)ethoxy]phenyl]methanone hydrochloride (see: Jones, ibid.)
*p < .05

An additional demonstration of the method of treating hyperlipidemia due to estrogen deprivation would be as follows: One hundred patients would be chosen, who are healthy postmenopausal women, aged 45–60, and who would normally be considered candidates for estrogen replacement therapy. This would include women with an intact uterus, who have not had a menstrual period for more than six months, but less than six years. Patients excluded for the study would be those who have taken estrogens, progestins, or corticosteroids.

Fifty women (test group) would receive 15–80 mg of a compound of formula I, for example, using Formulation 1, per day. The other fifty women (control group) would receive a matched placebo per day. The study would be a double-blind design. Neither the investigators nor the patients would know to which group each patient is assigned.

A baseline examination of each patient would include serum determination of cholesterol and tri-glyceride levels. At the end of the study period (six months), each patient would have their serum lipid profile taken. Analysis of the data would confirm a lowering of the serum lipids, for example, cholesterol and/or tri-glycerides, in the test group versus the control.

From the foregoing, it will be seen that this invention is one well adapted to attain all the ends hereinabove set forth together with advantages that are inherent to the invention. It will be understood that certain features and subcombinations are of utility and can be employed without reference to other features and subcombinations. This is contemplated by and within the scope of the claims. Because many possible embodiments can be made of the invention without departing from the scope thereof, it is to be understood that all matter herein set forth is to be interpreted as illustrative and not in a limiting sense.

We claim:

1. A compound of formula I wherein
$R^1$ is —H, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl);

$R^2$ is —H, —F, —Cl, —OH, —O($C_1$–$C_4$ alkyl), —OCOAr where Ar is phenyl or substituted phenyl, —O(CO)OAr where Ar is phenyl or substituted phenyl, —OCO($C_1$–$C_6$ alkyl), —O(CO)O($C_1$–$C_6$ alkyl), or —OSO$_2$($C_4$–$C_6$ alkyl);

$R^3$ and $R^4$ are, independently, —H, —F, —Cl, —CH$_3$, —OH, —O($C_1$–$C_4$ alkyl), —OCOAr where Ar is phenyl or substituted phenyl, —OCO($C_1$–$C_6$ alkyl), —O(CO)O($C_1$–$C_6$ alkyl), or —OSO$_2$ ($C_4$–$C_6$ alkyl), with the proviso that both $R^3$ and $R^4$ cannot be hydrogen;

n is 2 or 3; and $R^5$ is 1-piperidinyl;
or a pharmaceutically acceptable salt or solvate thereof.

2. A compound according to claim 1 wherein $R^1$ and $R^3$ each are —OH.

3. A compound according to claim 1 wherein $R^1$ is hydroxy and $R^3$ is methoxy.

4. A compound according to claim 1 wherein $R^1$ is methoxy and $R^3$ is hydroxy.

5. A compound according to claim 1 wherein n is two and $R^5$ is 1-piperidinyl.

6. A compound according to claim 1 wherein said salt thereof is the hydrochloride salt.

7. A compound according to claim 1 wherein $R^1$ and $R^3$ each are —OH, $R^5$ is piperidinyl, n is two, and said salt thereof is the hydrochloride salt.

8. A compound according to claim 1 wherein $R^1$ is hydroxy, $R^3$ is methoxy, $R^5$ is piperidinyl, n is two, and said salt thereof is the hydrochloride salt.

9. A compound according to claim 1 wherein $R^1$ is methoxy, $R^3$ is hydroxy, $R^5$ is piperidinyl, n is two, and said salt thereof is the hydrochloride salt.

10. A compound according to claim 1 selected from the group consisting of
1-[4-[2-(1-piperidinyl)ethoxy]phenoxy]-2-(3-methoxyphenyl)-6-methoxynaphthalene hydrochloride,
1-[4-[2-(1-piperidinyl)ethoxy]phenoxy]-2-(3-methoxyphenyl)naphthalene hydrochloride,
1-[4-[2-(1-piperidinyl)ethoxy]phenoxy]-2-(3-hydroxyphenyl)-6-hydroxynaphthalene hydrochloride,
1-[4-[2-(1-piperidinyl)ethoxy]phenoxy]-2-(3-hydroxyphenyl)naphthalene hydrochloride,
1-[4-[2-(1-piperidinyl)ethoxy]phenoxy]-2-(3-hydroxyphenyl)-6-methoxynaphthalene hydrochloride, and
1-[4-[2-(1-piperidinyl)ethoxy]phenoxy]-2-(3-methoxyphenyl)-6-hydroxynaphthalene hydrochloride.

11. A pharmaceutical formulation comprising a compound according to claim 1 in combination with a pharmaceutically acceptable carrier, diluent, or excipient.

12. A method of inhibiting bone loss or bone resorption comprising administering to a patient in need thereof an effective amount of a compound of claim 1, or a pharmaceutically acceptable salt or solvate thereof.

13. A method according to claim 12 wherein said bone loss or bone resorption is due to menopause or ovariectomy.

14. A method according to claim 12 wherein said patient is a postmenopausal female.

15. A method of lowering serum cholesterol comprising administering to a patient in need thereof an effective amount of a compound of claim 1, or a pharmaceutically acceptable salt or solvate thereof.

* * * * *